United States Patent
Greene et al.

(10) Patent No.: US 7,051,120 B2
(45) Date of Patent: May 23, 2006

(54) HEALTHCARE PERSONAL AREA IDENTIFICATION NETWORK METHOD AND SYSTEM

(75) Inventors: David P. Greene, Ossining, NY (US); Edith H. Stern, Yorktown Heights, NY (US); Barry E. Willner, Briarcliff Manor, NY (US); Philip Shi-lung Yu, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 660 days.

(21) Appl. No.: 10/033,806

(22) Filed: Dec. 28, 2001

(65) Prior Publication Data

US 2003/0125017 A1 Jul. 3, 2003

(51) Int. Cl.
*G06F 15/16* (2006.01)
*A61B 5/00* (2006.01)

(52) U.S. Cl. ............. 709/250; 709/221; 709/222; 600/301; 600/372; 600/485; 600/508

(58) Field of Classification Search ........ 709/220–222, 709/250; 600/301, 322–340, 372–397, 407, 600/485, 508, 544
See application file for complete search history.

(56) References Cited

U.S. PATENT DOCUMENTS

| | | | | |
|---|---|---|---|---|
| 6,104,913 | A * | 8/2000 | McAllister | 455/41.1 |
| 6,327,501 | B1 * | 12/2001 | Levine et al. | 607/27 |
| 6,346,886 | B1 * | 2/2002 | De La Huerga | 340/573.1 |
| 6,400,987 | B1 * | 6/2002 | Garberoglio | 607/18 |
| 6,409,674 | B1 * | 6/2002 | Brockway et al. | 600/486 |
| 6,532,368 | B1 * | 3/2003 | Hild et al. | 455/515 |
| 6,749,566 | B1 * | 6/2004 | Russ | 600/300 |
| 2002/0013538 | A1 * | 1/2002 | Teller | 600/549 |
| 2002/0026330 | A1 * | 2/2002 | Klein | 705/3 |
| 2002/0028988 | A1 * | 3/2002 | Suzuki et al. | 600/300 |
| 2003/0125017 | A1 * | 7/2003 | Greene et al. | 455/414 |

OTHER PUBLICATIONS

Wireless personal area networks in telemedical environment; Jovanov et al., Nov. 9-10, 2000. IEEE 0-7803-6449-x/00/$10.00. pp. 22-27.*

(Continued)

*Primary Examiner*—Kim Huynh
*Assistant Examiner*—Alan S. Chen
(74) *Attorney, Agent, or Firm*—Buckley, Maschoff & Talwalkar LLC; Stephen C. Kaufman

(57) ABSTRACT

A system, method, apparatus, and computer program code for delivering a treatment includes generating a personal area network associated with a patient, said personal area network transmitting a patient identifier associated with said patient, retrieving treatment data associated with said patient identifier, and operating a treatment device pursuant to said treatment data.

10 Claims, 11 Drawing Sheets

OTHER PUBLICATIONS

Web based monitoring of real time ECG data, Kong et al., Sep. 24-27, 2000. IEEE 0276-6547/00 $10.00. pp. 189-192.*

Pan Fact Sheet, Hi-Tech, High-Touch. IBM Almedan Research Center, Nov. 18-19, 1996. Http://www.almaden.ibm.com/cs/user/pan/pan.html. Print d out Dec. 10, 2004.*

1. The Body Electric, Gordon Bell, Communications of the ACM, Feb., 1997, p. 31-32.*

Zimmerman, T.G., "Personal Area Networks: Near-field intrabody communication", IBM Systems Journal, vol. 35, No. 3&4, 1996-MIT Media Lab, 0018-8670/96, © IBM. pp. 609-617.

* cited by examiner

| PATIENT IDENTIFIER 302 | PATIENT INFORMATION 304 | MEDICAL HISTORY 306 | CURRENT INFORMATION 308 |
|---|---|---|---|
| P1001 | Fred Johnson, age 42, 55 Elm Street, Anytown, NY 21002 | Diabetic; No penicillin | pneumonia |
| P1002 | Mary S. Jones, age 63 1 State St., Boston MA 17777 | High blood pressure | high blood pressure |
| P1003 | Sally Snead, age 72 9 Cadillo Lane, Albuquerque NM | Allergic to peanuts | liver transplant |

| TREATMENT IDENTIFIER 402 | PATIENT IDENTIFIER 404 | DATE 406 | TREATMENT INFORMATION 408 |
|---|---|---|---|
| T1001 | P1001 | 12/1/2001 | 20mg (medicine M1001), 2x daily |
| T1002 | P1002 | 12/1/2001 | blood pressure monitoring, 8x daily |
| T1003 | P1003 | 12/1/2001 | dialysis monitoring, 2x daily |

FIG. 8

HEALTHCARE PERSONAL AREA IDENTIFICATION NETWORK METHOD AND SYSTEM

FIELD OF THE INVENTION

This invention relates to the field of health care, and to the use of personal area networks in patient care.

BACKGROUND OF THE INVENTION

It is a continuing challenge in health care to ensure that intended health care actions are taken with respect to a given patient. With the proliferation of devices that collect information it has become increasingly difficult to associate patient data with the appropriate patient. Moreover, with the increased complexity of health care practices, even seemingly straightforward tasks such as matching a treatment action to a patient have become more difficult. Horror stories exist about patients receiving the wrong surgical or medical treatment due to failure to confirm the patient's identity or condition, or failure to confirm that the treatment or other health care action taken is the right one for the patient.

Thus, a need exists for action confirmation and validation for proposed health care practices, such as treatments. A need exists as well for improved ease of association between a patient and his or her medical data.

Personal area networks are known that are capable of handling communications using the electrochemical characteristics of a person. Such personal area networks have been used, for example, to uniquely identify persons for security purposes. Personal area networks have been disclosed, for example, in U.S. Pat. No. 6,104,913 to McAllister and in an article in IBM Systems Journal, Vol. 35, No. 3&4, 1996-MIT Media Lab, 0018-8670/96, copyright IBM, entitled Personal Area Networks: Near-Field Intrabody Communication, by T. G. Zimmerman. Both publications, together with all other patents, patent applications, and publications referenced herein are hereby incorporated by reference.

There is potential for personal area networks to solve the persistent problems of action confirmation, action validation, and the proper association of patient data.

SUMMARY OF THE INVENTION

Embodiments of the present invention provide a system, method, apparatus, and computer program code for delivering a treatment includes generating a personal area network associated with a patient, said personal area network transmitting a patient identifier associated with said patient, retrieving treatment data associated with said patient identifier, and operating a treatment device pursuant to said treatment data.

In some embodiments, the personal area network is generated using a transmitting device associated with the patient. In some embodiments, the treatment device is adapted to receive data from the transmitting device, including a patient identifier. In some embodiments, the personal area network is generated by a transmitter adapted to transmit signals through a body using electrical properties of said body. In some embodiments, the transmitter is configured as at least one of: a bracelet, a necklace, a card, a ring, and a molecular tag.

In some embodiments, delivering a treatment further includes performing a verification based at least in part on the patient identifier and the treatment data. In some embodiments, the verification includes determining if the treatment data is consistent with information about said patient. In some embodiments, the verification includes determining if said treatment data is consistent with accepted treatment protocols.

In some embodiments, the treatment device includes a communications device and a sensor, each in communication with a processor for processing data received by the communications device. In some embodiments, the communication device is adapted to send and receive data over the personal area network. In some embodiments, the communication device is adapted to communicate with a controller via a communications network.

In some embodiments, the controller includes a communications device and a mass storage device each in communication with a processor, said mass storage device storing patient data and treatment data.

In some embodiments, delivering a treatment further includes operating the treatment device to perform at least one of: refraining from delivering full treatment; signaling an alarm; signaling an alert; not performing treatment; modifying treatment; initiating an application; initiating a human interaction; recording initiation of treatment; recording data; performing intermediate steps; and concluding treatment. In some embodiments, delivering a treatment further includes alerting a provider of a condition of said patient. In some embodiments, the treatment device is further in communication, via said personal area network, with a second treatment device. In some embodiments, the patient identifier is generated using a security protocol to maintain patient anonymity. In some embodiments, delivering treatment further includes determining a diagnosis of said patient prior to said operating said treatment device.

Embodiments of the present invention also provide a system, method, apparatus, and computer program code for delivering a treatment to a patient, including: detecting, via a personal area network associated with the patient, a patient identifier, associating the patient identifier with a treatment, the treatment defined by a set of treatment data, and determining if the treatment should be delivered to the patient. In some embodiments, the determining also includes retrieving patient data including medical data regarding the patient, and comparing the patient data with the set of treatment data to determine if a conflict exists. In some embodiments, the treatment is selected from the group consisting of: administering a shot, an oral medicine, an intravenous drip, a cut, an inflation, an electrical impulse, a pacemaker, an electroshock, a catheterization, insertion of a stent, and insertion of a tube.

In some embodiments, at least one of the patient data and the treatment data are stored in a device in communication with the treatment device over a communications network. In some embodiments, at least one of the patient data and the treatment data are stored in a network device in communication with the treatment device over the personal area network.

Embodiments of the present invention also provide a system, method, apparatus, and computer program code for delivering a treatment to a patient including: detecting, using a treatment device, a patient identifier, the patient identifier transmitted over a personal area network associated with the patient; retrieving patient information associated with the patient identifier; and forwarding treatment data associated with the patient identifier to the treatment device.

Embodiments of the present invention also provide a system, method, apparatus, and computer program code for system for providing health care, including: a personal area network for facilitating communication of data via a patient's body, and an intelligent device for facilitating a health care service via the communication of data.

Embodiments of the present invention also provide a system, method, apparatus, and computer program code for handling data associated with a health care patient, including: associating a patient with a personal area network, recording data associated with the patient, and associating the data with a record for the patient in a database. In other embodiments, a system, method, apparatus, and computer program code for facilitating a health care service, include: providing a processor for a personal area network, and configuring the processor to facilitate communication with an intelligent health care device.

Embodiments of the present invention also provide a system, method, apparatus, and computer program code for treating a patient, including: generating a personal area network associated with the patient, the personal area network generated by a transmitting device; establishing communication between the transmitting device and a treatment device via the personal area network; and transmitting treatment data between the transmitting device and the treatment device. In some embodiments, the transmitting device checks to see if the treatment device and/or the treatment data are appropriate. In some embodiments, the treatment device checks to see if the patient and/or the treatment data are appropriate.

With these and other advantages and features of the invention that will become hereinafter apparent, the nature of the invention may be more clearly understood by reference to the following detailed description of the invention, the appended claims and to the several drawings attached herein.

BRIEF DESCRIPTION OF THE DRAWINGS

FIG. 7 is a tabular representation of a portion of a patient database according to an embodiment of the present invention;

FIG. 8 is a tabular representation of a portion of a treatment database according to an embodiment of the present invention;

DETAILED DESCRIPTION

Applicants have recognized that there is a need for a system, method, apparatus, and computer program code for operating a personal area network (PAN) for healthcare applications. Applicants have further recognized that there is a need for systems, methods, apparatus, and computer program code for action confirmation and validation for proposed health care practices, such as treatments. Applicants have also recognized a need for improved ease of association between a patient and his or her medical data.

Figure 1:
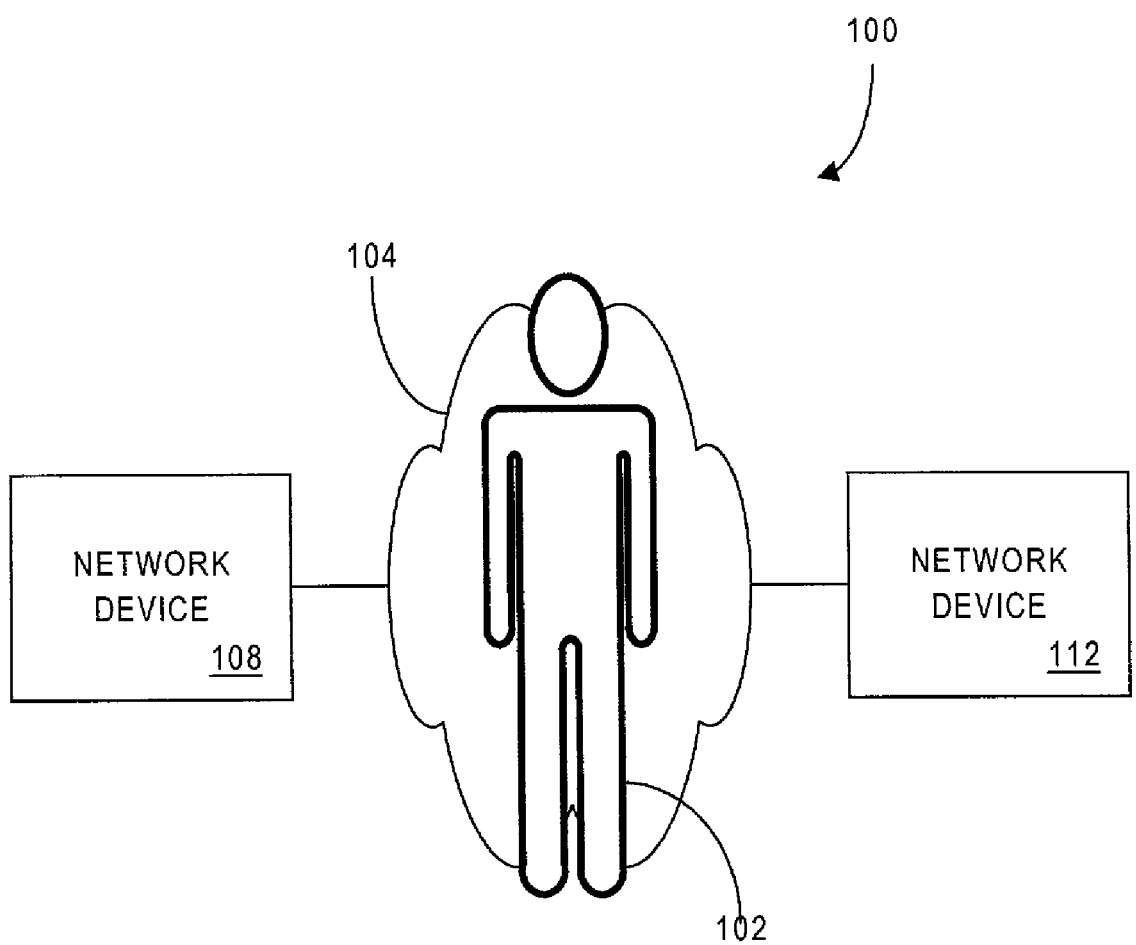
FIG. 1 is a block diagram of a system pursuant to embodiments of the present invention.

Referring first to FIG. 1, a system 10 for administering healthcare according to embodiments of the present invention is shown. As depicted, system 100 includes a patient 102 (who is to receive treatment or diagnosis using features of the present invention). Pursuant to embodiments of the present invention, a personal area network (PAN) 104 is created which is associated with patient 102. PAN 104 may be configured to facilitate communication between devices, such as, for example network devices 108 and 112. As will be described further below, any of a number of different types of network devices 108, 112 may be utilized, such as, for example, medical treatment and diagnostic devices having the capability to transmit and/or receive data via PAN 104. In some embodiments, one or more network devices 108, 112 will store data and other information associated with a particular PAN 104 (and thus, with a particular patient 102). Other network devices 108, 112 may store treatment, diagnostic, or other data which may be associated with a number of different patients (e.g., a treatment device may store information that may be used to treat a large number of patients).

In some embodiments, PAN 104 allows communication of data via the electrochemical properties of the body of patient 102, including differential levels of electrical fields between areas close to the body and areas slightly further from the body. Embodiments of a PAN are disclosed in U.S. Pat. No. 6,104,913, incorporated herein by reference for all purposes. Through establishment and manipulation of PAN 104, embodiments of the present invention establish communication among a wide range of health care devices that are equipped for data storage, communication or manipulation, when those devices are in proximity to the PAN 104. Further, embodiments of the present invention utilize features of PAN 104 to uniquely identify the patient 102 on which PAN 104 is disposed, such as by a patient identifier that is unique to patient 102 and/or PAN 104.

According to some embodiments, PAN 104 facilitates the transmission of data among electronic devices deployed on or near patient 102 by capacitively coupling pico-amp currents through the body. In some embodiments, a low-frequency carrier is used so no energy is propagated. The natural salinity of the human body makes it a conductor of electrical current. PAN 104 takes advantage of this conductivity by creating an external electric field that passes a very small current through the body, over which data is carried. The current used can be as low as one-billionth of an ampere (one nanoamp), which is lower than the natural currents already in the body.

Data can be transmitted using PAN 104 for a wide variety of purposes as disclosed herein. PAN 104 may be uniquely associated with a particular patient 102 in a number of ways, including, for example, the use of a unique identifier, or the use of biological or chemical characteristics of the patient (e.g., so that it is not necessary to access processing or data capabilities that are separated from the patient). Unique identification of patient 102 ensures that a particular treatment or other processing may be directed to a particular patient. Pursuant to some embodiments of the present invention, accessing data carried by PAN 104 for a particular patient is a reliable way of confirming that the correct patient has been reached, because the PAN remains disposed on the patient and can be constructed to have characteristics that are unique to that patient/PAN combination.

In some embodiments, one or more network devices 108, 112 in PAN 104 is configured with data storage, manipulation, retrieval and communication capabilities, thereby allowing devices coupled to PAN 104 to interact with incoming data from other health care devices in proximity to the PAN 104. For example, devices in communication with PAN 104 can receive a message of a proposed health care action for a patient and can confirm that a particular patient 102 about which PAN 104 is disposed is the correct patient for that proposed action (e.g., by matching a patient identifier sent by a health care device to the patient identifier stored in association with the PAN 104).

Network devices 108, 112 in communication via PAN 104 can also store data and instructions about patient 102 (such as prohibitions against certain treatment or diagnostic actions), that can be accessed and retrieved upon receipt of inquiry messages (e.g., such as messages regarding a proposed treatment). For example, one or more network devices accessible to PAN 104 can store a treatment order that patient 102 will receive "no milk products" and can signal an alert or alarm if a message is transmitted, such as from a food tray or food container in proximity to PAN 104, that the food contains milk products. Thus, network devices associated with PAN 104 can store and manipulate necessary data to compare restrictions to proposed actions, such as food restrictions to food, drug restrictions to drugs, and activity restrictions to proposed activities.

Health care actions taken in response to the system 100 disclosed herein should be understood to encompass not only affirmative treatment actions, but other actions such as doing nothing, signaling an alarm or alert, not performing treatment, modifying treatment, applying a restriction to prevent an action, declining an action based on a counter-order, applying a condition to an action (such as compatibility of the action with a criterion, such as a match between treatment and diagnosis), initiating an application, initiating a human interaction, recording data, recording conditions, recording initiation of treatment, intermediate steps, and conclusion of treatment.

In some embodiments, PAN 104 is set up with one network device 108 serving as a transmitting device 108 and another network device 112 serving as a receiving device 112. The transmitting device and the receiving device may establish fields through the use of electrodes. For example, an electrode of the transmitter that is closer to the body of patient 102 may have a lower impedance to the body than a second electrode facing toward the surrounding environment. In this manner, a transmitting device may impose an oscillating potential on the body of the patient 102, relative to the earth ground, causing electrical fields around and near the patient.

The impedance of electrodes of the receiver is also asymmetrical to the body and the environment, allowing the displacement current from the electrical fields between the body and the electrode and the body and the ground to be detected. Since the impedance between the receiver electrodes is nonzero, a small electric field exists between them. As a result, a network device functioning as a transmitter 108 can capacitively couple to a network device acting as a receiver 112 through the body. Those skilled in the art will recognize that a number of different types of transmitter and receiver devices may be used to establish and communicate via PAN 104.

Network devices functioning as a PAN 104 transmitter 108 can be embodied in any of a wide range of structure or devices, including, for example, an ID bracelet, a belt, an anklet, a ring, eyeglasses, an earpiece, an internal device, a necklace, a device taped or otherwise affixed to the body, a wrap, a sling, a prosthetic, a pocket-device, or any other device suitable for wearing or affixing to or in the body.

Network devices functioning as a PAN 104 receiver 112 can be embodied in any of a wide range of structure or devices, including many intelligent devices that are capable of processing and communications functions, such as, for example: an intelligent- or microprocessor-controlled IV, blood pressure meter, EKG, EEG, fluid meter, needle, food tray, operating table, surgical light, operating light, scalpel, knife thermometer, an IV, a blood pressure cuff, a fluid sensor, a patch, a vial, a bottle, a blade, a clamp, a stent, a prosthesis, a catheter, a tube, an intubator, a medicine bottle, sphygmomenometer, a toxicity screening device, a chemical sensor, a spectrometer, a respiration rate measurement device, an MRI, a CT device, or an X-ray device. Any one of these devices may communicate data with the PAN 104 to facilitate provision of health care. Other network devices may also function as a PAN 104 receiver 112 such as, for example, a hospital computer system, diagnostic devices, or other treatment devices.

Figure 2:
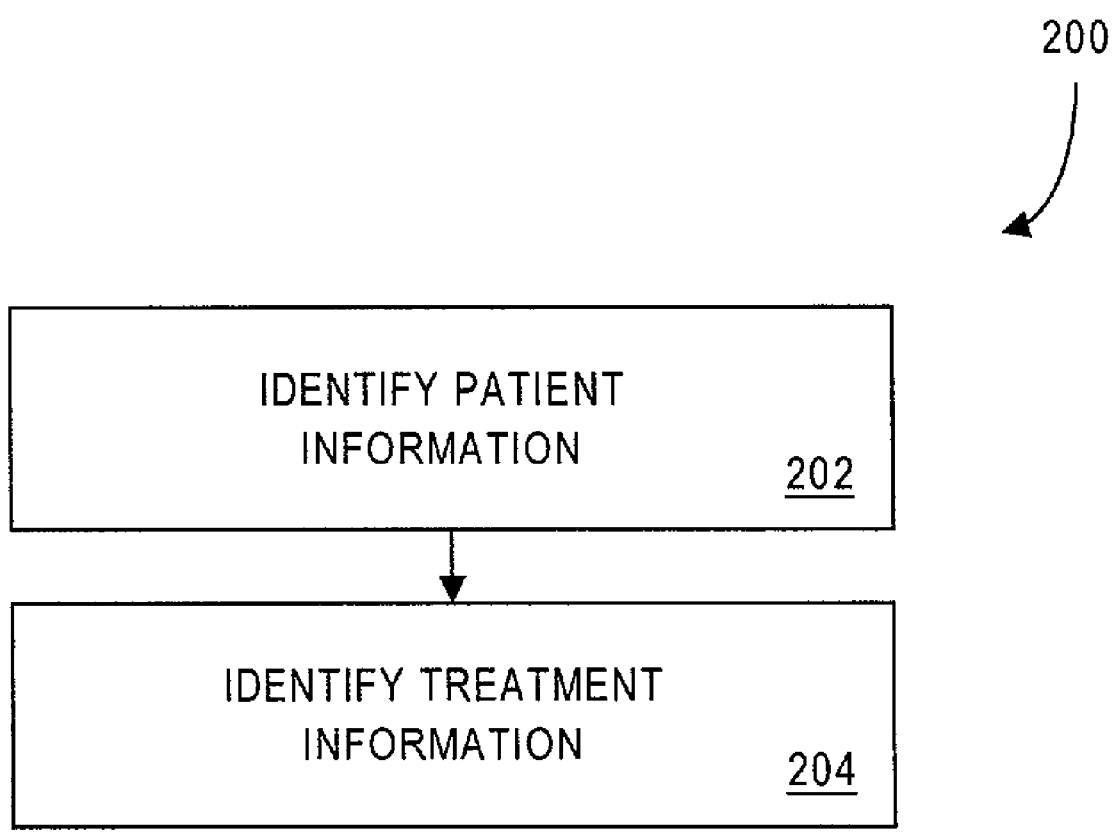
FIG. 2 is a diagram depicting an identification process of the system of FIG. 1 according to one embodiment of the invention.

A process 200 for utilizing system 100 to provide health care treatment is shown in FIG. 2. Process 200 will be described to illustrate certain features of embodiments of the present invention. The steps of process 200 and other processes described herein may be performed in any order practicable. Process 200 begins at 202 where patient information is identified. In some embodiments, this identification is performed using PAN 104. For example, a patient who is to receive treatment at a health care facility may be provided with one or more network devices 108, 112 adapted to establish a PAN 104 for the patient. In some embodiments, the patient receives a portable transmitter configured, for example, as a bracelet, which establishes a low voltage carrier network about the patient. In some embodiments, the transmitter device includes a unique identifier, which is associated with the patient. In some embodiments, the PAN 104 which is established has unique identifying characteristics which are used at step 202 to identify the patient. In some embodiments, this patient identifier is received by one or more network devices acting as receiving devices. For example, assume the patient is about to receive an injection, and has a PAN 104 established for him. An intelligent shot (e.g., having the ability to receive data via PAN 104) may receive the patient identifier via PAN 104.

Processing at 202, in some embodiments, further includes using a patient identifier to retrieve patient information from a patient database or from some other datastore. For example, information retrieved at 202 may include an identification of the patient's name and an identification of health care information regarding the patient (e.g., any allergies, special instructions, etc.).

Processing continues at 204 where system 100 operates to identify treatment information. In some embodiments, this treatment information is identified based at least in part on the patient information identified at 202. In the example where the patient is to receive an injection and the patient identifier has been received by the intelligent shot, the patient identifier may be used to retrieve patient information as well as treatment information to determine if the correct dosage of the correct medication is about to be delivered. The result is a system which facilitates the accurate delivery of treatment and diagnostic care. The system reduces or eliminates the possibility for miscommunication between doctors and their staff.

Figure 3:
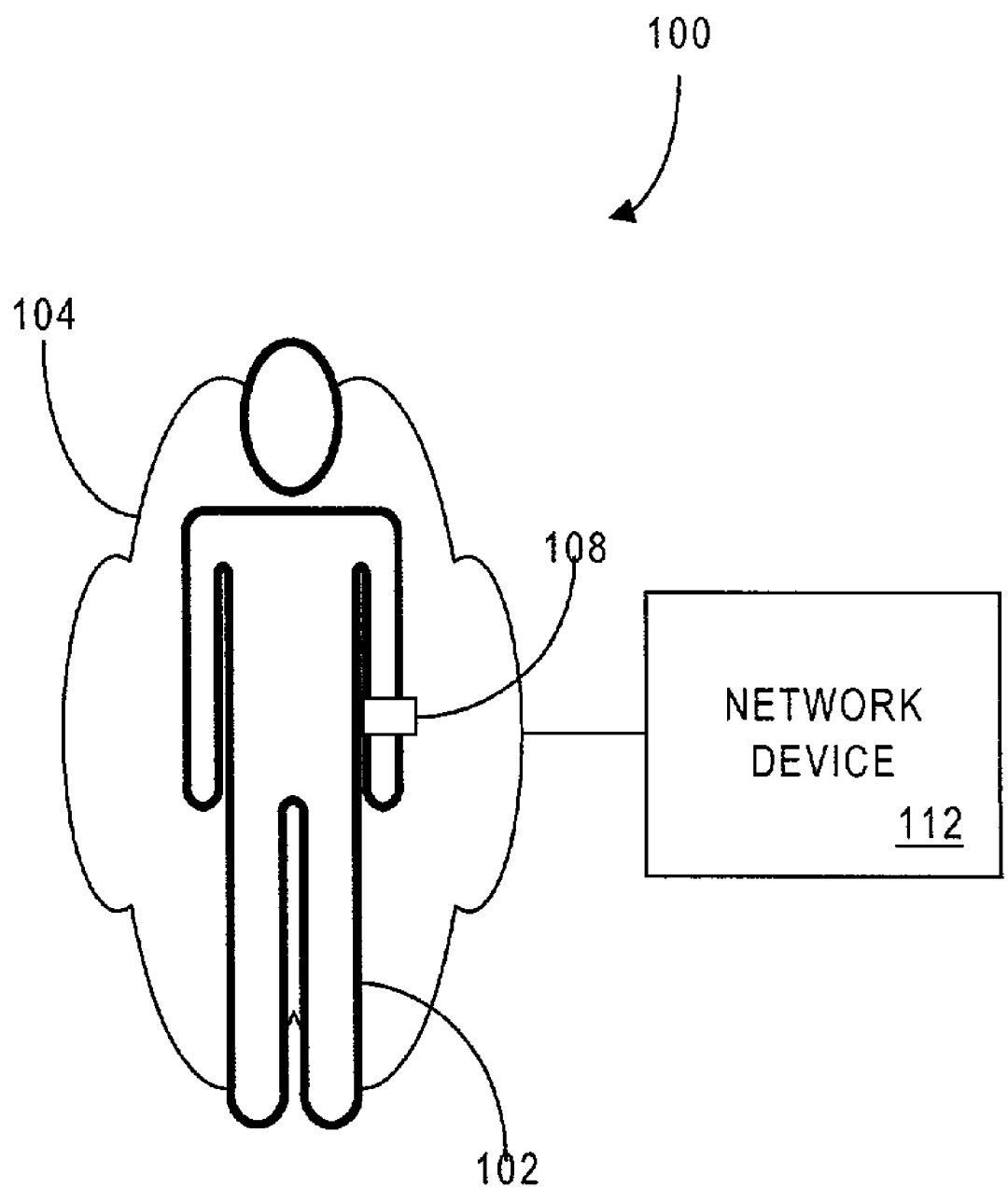
FIG. 3 is a block diagram of an embodiment of the system of FIG. 1.

System 100 may be configured in any of a number of different manners. As described above, one or more network devices 108 may be configured as transmitting devices used to set up the field of the PAN 104. An example of such an embodiment is depicted in FIG. 3, where a network device 108 is configured as a bracelet or other small device associated with a particular patient.

Figure 4:
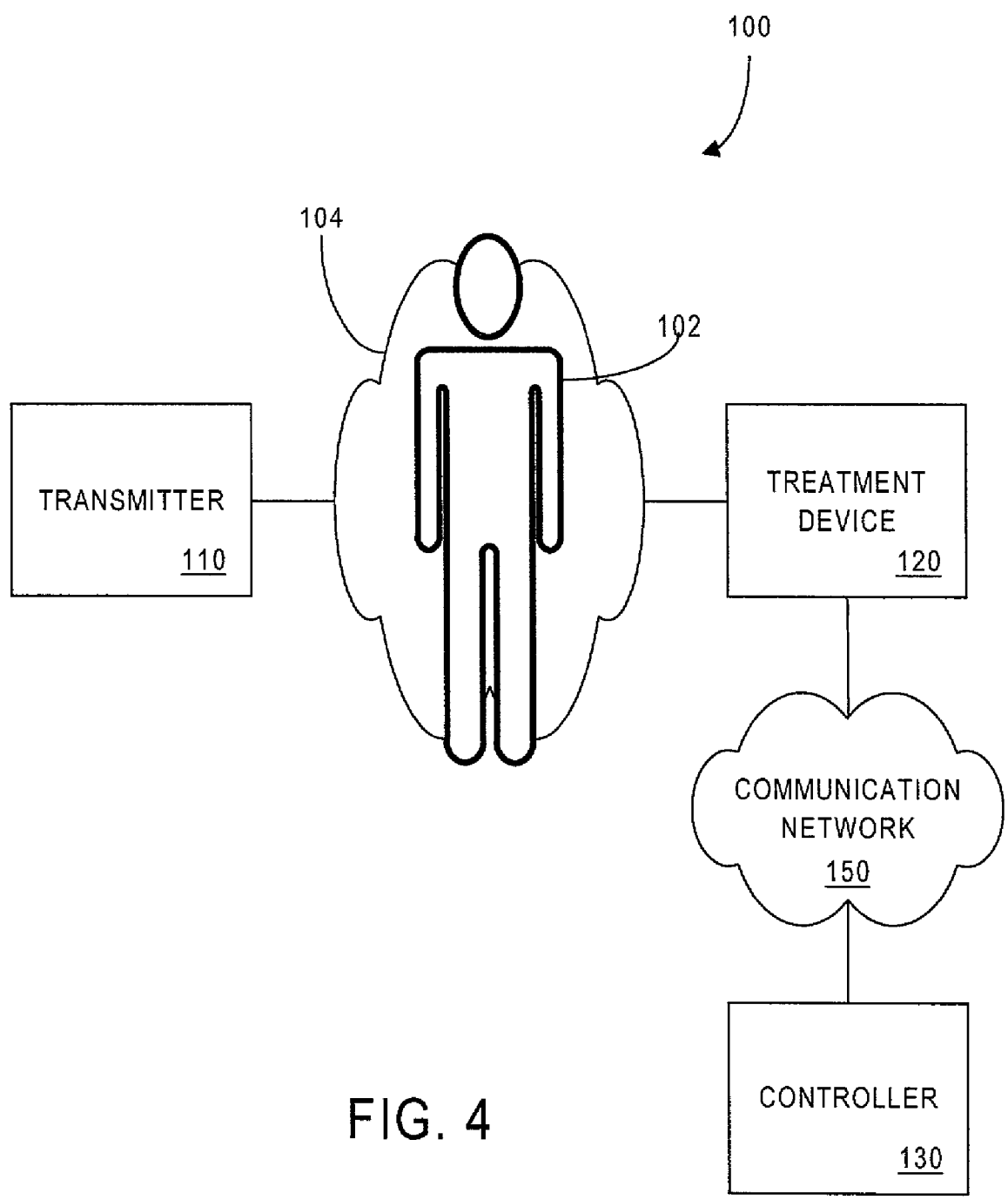
FIG. 4 is a block diagram of an embodiment of the system of FIG. 1.

Referring to FIG. 4, an embodiment is shown where one or more network devices are in communication with other devices through a second communication network 150. For example, as depicted in FIG. 4, system 100 may include a PAN 104 set up and disposed about a patient 102, allowing communication between one or more network devices (depicted as a transmitter 110 and a treatment device 120). Although only one transmitter 110 and one receiver 120 are shown, those skilled in the art will recognize that any of a number of different such devices may be provided.

Treatment device 120 is shown in communication with a controller 130 via a communication network 150. In some embodiments, transmitter 110 and other devices may also be in communication via communication network 150. As an example, treatment device 120 may be an MRI machine adapted to receive information via PAN 104, and also adapted to be in communication with a central treatment device (controller 130). The result is a system which allows centralized treatment planning and control, with widely-disseminated devices capable of confirming and identifying treatment delivery.

Communication network 150 may be any of a number of different types of commonly-used networks, such as a Local Area Network (LAN), a Metropolitan Area Network (MAN), a Wide Area Network (WAN), a proprietary network, a Public Switched Telephone Network (PSTN), a Wireless Application Protocol (WAP) network, a wireless network, a cable television network, or an Internet Protocol (IP) network such as the Internet, an intranet or an extranet. Moreover, as used herein, communications include those enabled by wired or wireless technology.

Controller 130 may be configured as any of a number of different types of computing devices. In general, controller 130 is a computing device such as: a Personal Computer (PC), a portable computing device such as a Personal Digital Assistant (PDA), a wired or wireless telephone, a one-way or two-way pager, a kiosk, an interactive television device, or any other appropriate storage and/or communication device.

Figure 5:
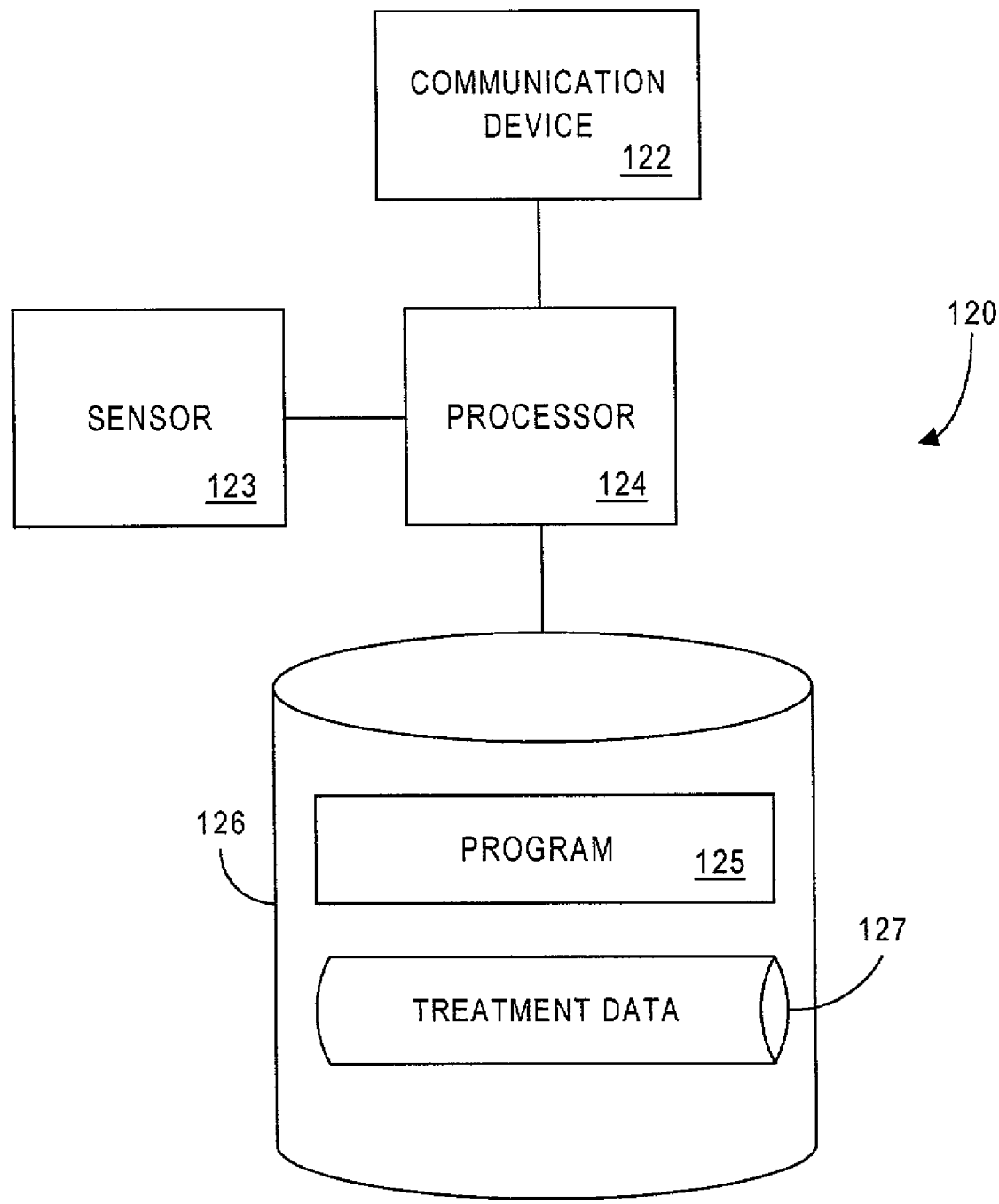
FIG. 5 is a block diagram depicting an embodiment of a treatment device used as a receiver in the system of FIG. 1.

FIG. 5 illustrates an embodiment of a treatment device 120 which may be operated in conjunction with PAN 104 of system 100. In general, treatment device 120 may be operated by health care personnel trained to deliver treatment or diagnostic care. As described above, treatment device 120 may be any of a number of different treatment or diagnostic devices. In addition, treatment device 120 may be provided with additional functionality allowing it to send and/or receive data via PAN 104 and/or communications network 150.

For example, treatment device may be configured with a processor 124, which may be any of a number of suitable processing devices, such as one or more Intel® Pentium® processors. Processor 124 is coupled to a communication device 122 through which processor 124 communicates with other devices, such as, for example, other network devices coupled to PAN 104 (e.g., such as a receiver used to set up the PAN). Processor 124 may also communicate with other devices via communications network 150 (e.g., such as controller 130).

In some embodiments, treatment device 120 may also be provided with one or more sensor devices 123 in communication with processor 124 for sensing information relevant to health care. By way of example, sensor device 123 may be a thermometer, blood pressure sensor, oxygen sensor, chemical sensor, light sensor, electromagnetic sensor, electrical sensor, pulse sensor, respiration sensor, or any other sensor capable of sensing a condition of a patient or environment that may be relevant to health care for the patient 102. In any of these cases, sensor 123 may be an intelligent sensor, with processing and communications capabilities, as well as sensing capabilities.

Communication device 122 may include hardware and software to facilitate communication with other devices using wired or wireless techniques, or a combination of different techniques. For example, communication device 122 may be one or more of: a network adapter, a modem, a Bluetooth device, electrodes adapted to receive low voltage signals via a PAN, etc. In one embodiment, communication device 122 facilitates communication with other devices over a network such as the Internet. Processor 124 may also be in communication with one or more input and output devices (not shown) as are known in the art (such as, for example, a keyboard, mouse, microphone, monitor, printer, etc.).

Processor 124 is also in communication with a data storage device 126. Data storage device 126 comprises an appropriate combination of magnetic, optical and/or semiconductor memory, and may include, for example, Random Access Memory (RAM), Read-Only Memory (ROM), a compact disc and/or a hard disk. Processor 124 and data storage device 126 may each be, for example: (i) located entirely within a single computer or other computing device; or (ii) connected to each other by a remote communication medium, such as a serial port cable, telephone line or radio frequency transceiver.

Data storage device 126 stores a program 125 for controlling processor 124. Processor 124 performs instructions of program 125, and thereby operates in accordance with the present invention, and particularly in accordance with the methods described in detail herein. For example, program 125 may include one or more treatment applications, diagnostic applications, record keeping applications, communications applications, data storage applications, and other applications suitable for health care actions. There are many examples of health care applications. Examples of actions that can be executed by program 125 include performing treatment, signaling an alarm or alert, halting treatment, modifying treatment, initiating another application, initiating human interaction, recording treatment, recording initiation of treatment, taking intermediate steps, concluding treatment, applying a restriction to a proposed treatment, checking a treatment for conflict with orders, not taking action, or the like.

Program 125 may be stored in a compressed, uncompiled and/or encrypted format. Program 125 furthermore includes program elements that may be necessary for allowing processor 124 to interface with computer peripheral devices, such as an operating system and "device drivers". Appropriate program elements are known to those skilled in the art, and need not be described in detail herein.

According to an embodiment of the present invention, the instructions of program 125 may be read into a main memory from another computer-readable medium, such as from a ROM to RAM. Execution of sequences of the instructions in program 125 causes processor 124 to perform the process steps described herein. In alternative embodiments, hard-wired circuitry may be used in place of, or in combination with, software instructions for implementation of the processes of the present invention. Thus, embodiments of the present invention are not limited to any specific combination of hardware and software.

Data storage device 126 also store one or more databases or datastores, such as, for example, specific treatment data associated with treatment device 120 (e.g., a treatment device may store an identifier uniquely identifying itself, and configuration information identifying the configuration of the device, as well as other data which may be useful in identifying, assessing, and delivering treatment).

Figure 6:
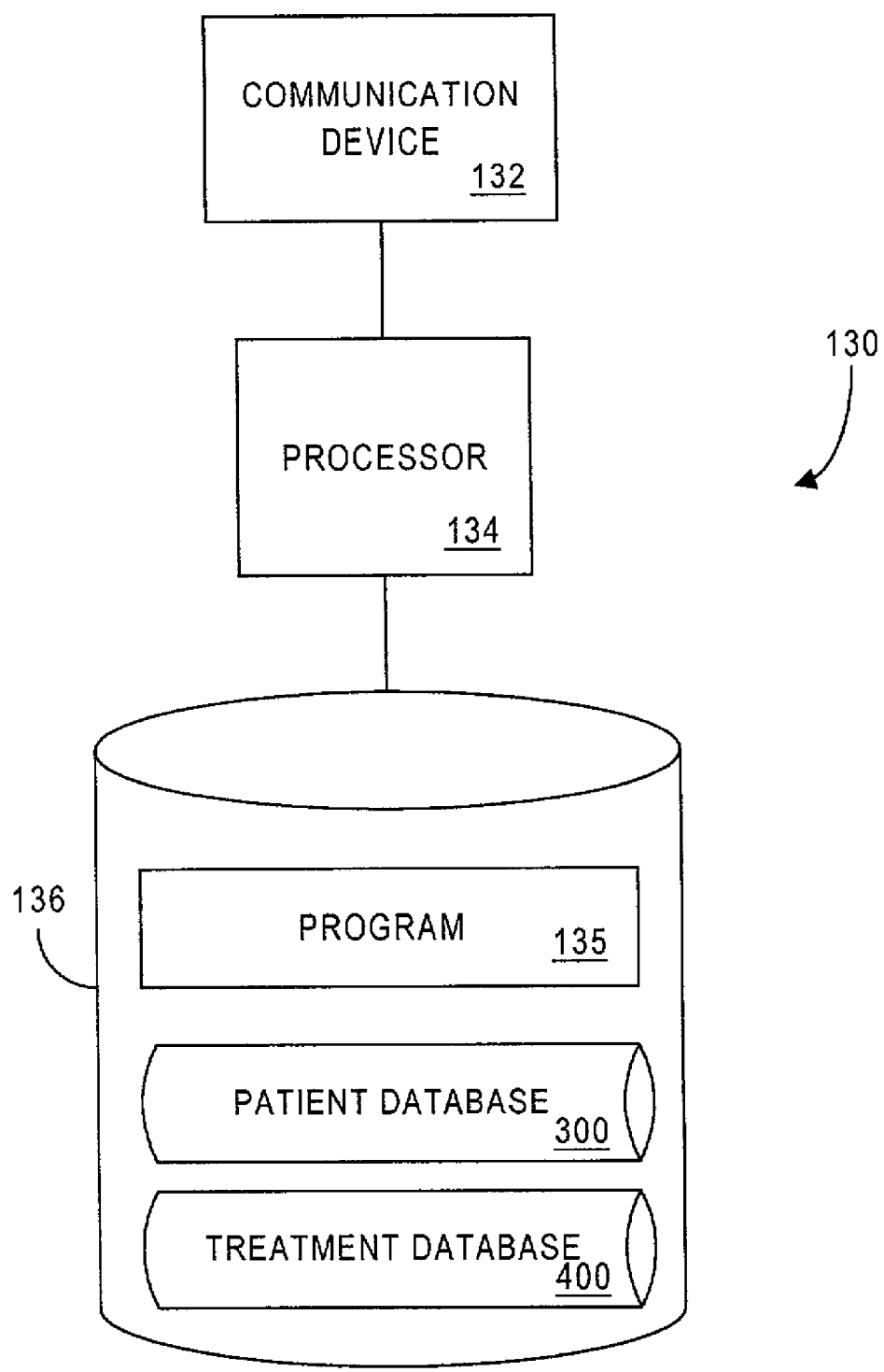
FIG. 6 is a block diagram depicting an embodiment of a controller used in the system of FIG. 4.

Referring now to FIG. 6, an embodiment of a controller 130 (e.g., as depicted in the system 100 of FIG. 4) is shown. In general, controller 130 may be operated by health care personnel trained to deliver treatment or diagnostic care. In some embodiments, controller 130 consists of one or more hospital or health care systems used to track, store, manipulate, or otherwise utilize patient and treatment information.

Controller 130 may be configured with a processor 134, which may be any of a number of suitable processing devices, such as one or more Intel® Pentium® processors. Processor 134 is coupled to a communication device 132 through which processor 134 communicates with other devices, such as, for example, one or more treatment devices or other network devices 108, 112.

Communication device 132 may include hardware and software to facilitate communication with other devices via communication network 150 using wired or wireless techniques, or a combination of different techniques. For example, communication device 132 may be one or more of: a network adapter, a modem, a Bluetooth device, electrodes adapted to receive low voltage signals via a PAN, etc. In one embodiment, communication device 132 facilitates communication with other devices over a network such as the Internet. Processor 134 may also be in communication with one or more input and output devices (not shown) as are known in the art (such as, for example, a keyboard, mouse, microphone, monitor, printer, etc.).

Processor 134 is also in communication with a data storage device 136. Data storage device 136 comprises an appropriate combination of magnetic, optical and/or semiconductor memory, and may include, for example, Random Access Memory (RAM), Read-Only Memory (ROM), a compact disc and/or a hard disk. Processor 134 and data storage device 136 may each be, for example: (i) located entirely within a single computer or other computing device; or (ii) connected to each other by a remote communication medium, such as a serial port cable, telephone line or radio frequency transceiver.

Data storage device 136 stores a program 135 for controlling processor 134. Processor 134 performs instructions of program 135, and thereby operates in accordance with the present invention, and particularly in accordance with the methods described in detail herein. Program 135 may be stored in a compressed, uncompiled and/or encrypted format. Program 135 furthermore includes program elements that may be necessary for allowing processor 134 to interface with computer peripheral devices, such as an operating system and "device drivers". Appropriate program elements are known to those skilled in the art, and need not be described in detail herein.

According to an embodiment of the present invention, the instructions of program 135 may be read into a main memory from another computer-readable medium, such as from a ROM to RAM. Execution of sequences of the instructions in program 135 causes processor 134 to perform the process steps described herein. In alternative embodiments, hard-wired circuitry may be used in place of, or in combination with, software instructions for implementation of the processes of the present invention. Thus, embodiments of the present invention are not limited to any specific combination of hardware and software.

Data storage device 136 may also store one or more databases or datastores, such as, for example, a patient database 300 and a treatment database 400. Other databases may also be provided, such as, for example, diagnostic databases, treatment or disorder history databases, insurance databases, etc. Each of these databases will be described further below in more detail. Those skilled in the art will recognize that controller 130 may store or otherwise access other information as well.

Each of the databases referred to in FIG. 6 will now be described by referring to FIGS. 7–8. While the databases are shown as being stored at, or accessible by, controller 130, portions of or all of the data in one or more of the databases may be stored at or accessible to other devices in the system. For example, in some embodiments, some or all of the data is stored at individual network devices 108, 112 (e.g., such as individual treatment devices).

As will be understood by those skilled in the art, the schematic illustrations and accompanying descriptions of the databases presented herein are exemplary arrangements for stored representations of information. A number of other arrangements may be employed besides those suggested by the tables shown. Similarly, the illustrated entries of the databases represent exemplary information only; those skilled in the art will understand that the number and content of the entries can be different from those illustrated herein.

Referring to FIG. 7, a table is shown representing a patient database 300 that may be stored at, or accessible by, controller 130 according to an embodiment of the present invention. In some embodiments, some or all of the data in patient database 300 may be stored at, or otherwise accessible by, individual devices in communication with PAN 104.

As depicted in FIG. 7, the table includes entries identifying a number of different patients that have been identified as requiring treatment or diagnosis using systems of the present invention. Patients identified in patient database 300 may include individuals who are scheduled for treatment or diagnosis or individuals who may visit a particular treatment facility (e.g., patient database may include information identifying all individuals registered in a particular HMO or other group). This information may be stored in database 300 when a patient becomes a member of a registered group, or it may be stored once a facility learns that a particular individual is seeking or is scheduled for treatment or diagnosis.

The table shown in FIG. 7 defines a number of fields 302–308 for each of the entries. In the embodiment depicted, the fields specify: a patient identifier 302, patient information 304, a medical history 306, and current information 308. Other fields and combinations of fields may also be used to provide and access information about different patients and their associated medical requirements and information.

Patient identifier 302 may be, for example, an alphanumeric code or other information that is associated with and used to identify a patient who will or may receive treatment pursuant to embodiments of the present invention. Patient identifier 302 may be generated by, for example, controller 130 (FIG. 3) or it may be provided by a patient or some other entity. In some embodiments, the patient identifier is the patient's social security number or health insurance identifier. Other information used to identify the patient may be provided at 304, such as, for example, the patient's age, address, next of kin, insurance information, etc.

Medical history 306 may be, for example, information identifying significant medical information about the patient identified by patient identifier 302 (e.g., such as whether the patient has any serious allergies, specific drug needs, health concerns, etc.). This information may be used by devices configured using embodiments of the present invention to ensure that appropriate treatment is provided. Current information 308 may be, for example, information identifying current treatment information regarding the patient. For example, current information 308 may indicate that the patient is currently undergoing treatment for a particular condition. Again, this information may be used by treatment devices configured pursuant to the present invention to administer appropriate treatment. Other information may also be provided in patient database 300 to further identify the patient, his or her medical history, and his or her treatment needs.

Referring to FIG. 8, a table is shown representing a treatment database 400 that may be stored at, or accessible by, controller 130 according to an embodiment of the present invention. In some embodiments, some or all of the data in treatment database 400 may be stored at, or otherwise accessible by, individual devices in communication with PAN 104 (e.g., treatment information may be stored at, or accessible by, individual treatment devices in communication with PAN 104).

As depicted in FIG. 8, the table includes entries identifying a number of different treatments that have been identified as requiring administration using systems of the present invention. Treatments identified in treatment database 400 may include, for example, individual courses of treatment that are scheduled for particular patients visiting a particular treatment facility. This information may be stored in database 400 when a physician or other qualified medical technician diagnoses and prescribes a course of treatment or diagnosis for a particular patient.

Treatment identifier 402 may include information uniquely identifying a particular treatment which has been prescribed. Patient identifier 404 may include information uniquely identifying a particular patient for whom a particular treatment is to be delivered. Date 406 includes information identifying a particular time or date on which (or by which) the treatment identified by treatment identifier 402 is to be delivered. Treatment information 408 includes information describing a particular treatment to be delivered. Any of a number of different types of information may be provided at 408, including, for example, dosages, frequencies, etc.

Figure 9:
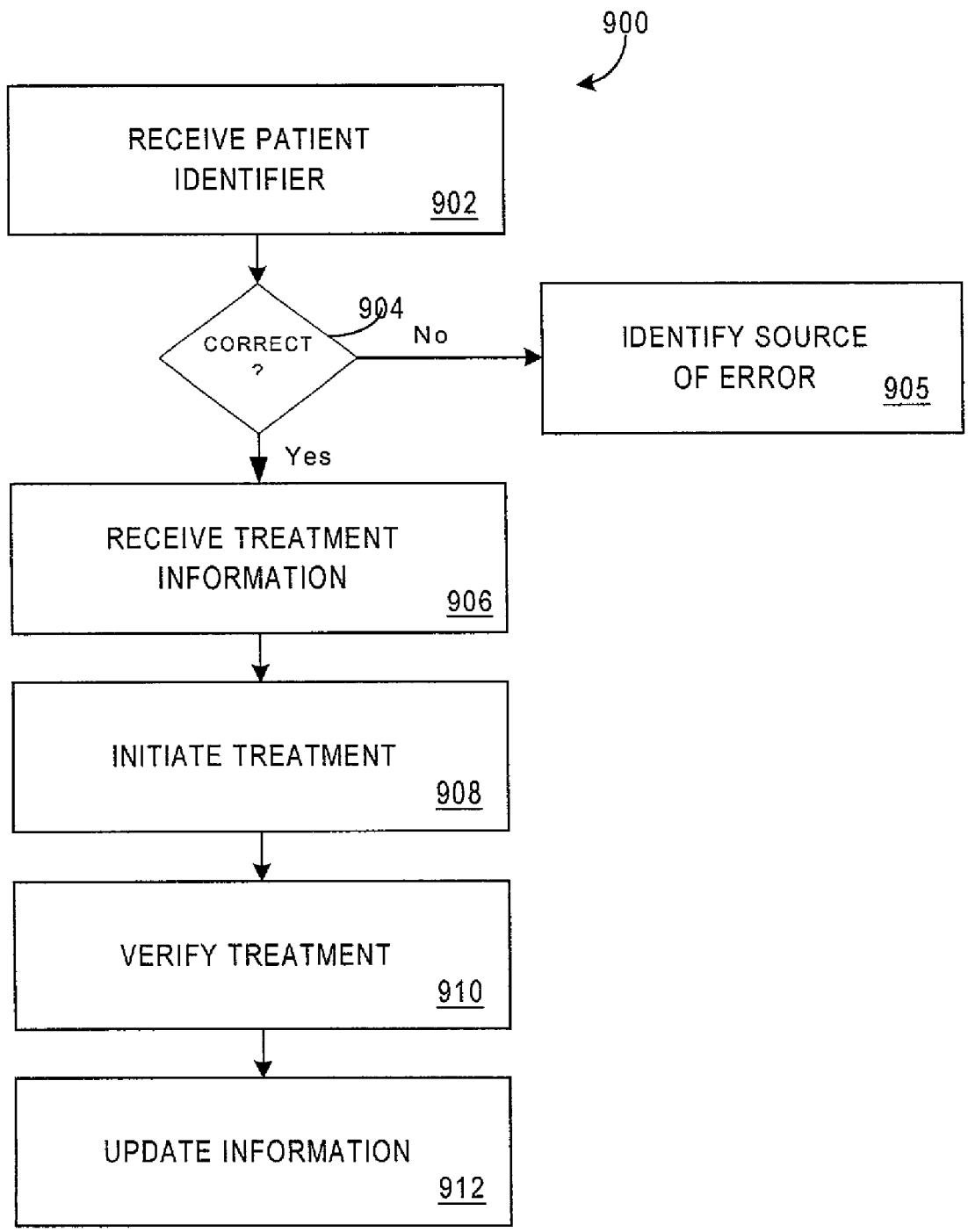
FIG. 9 is a flow diagram depicting a treatment process according to one embodiment of the present invention.

Treatment processes which may be implemented using system 100 will now be described by first referring to FIG. 9, where a treatment process 900 pursuant to one embodiment of the present invention is shown. Process 900 may be performed using devices as depicted in, for example, FIG. 4.

Process 900 begins at 902 where treatment device 120 receives a patient identifier from transmitter 110 via PAN 104. For example, treatment device may be any of a number of different types of devices as described above which are adapted to deliver treatment or diagnostic health care to a patient. At 904, treatment device 120 performs processing to determine whether the patient identifier accurately identifies the patient for whom treatment is intended. This may be performed by comparing the patient identifier to stored information about a particular course of treatment (which may be stored at, for example, treatment device 120 and/or controller 130). Those skilled in the art will recognize that process 900 may also be initiated by first identifying an identifier of the treatment device 120 to determine if the treatment device 120 should be associated with the patient 102.

If processing at 904 indicates that the patient is not the intended patient, or if processing at 904 indicates that the treatment to be provided by treatment device 120 is not intended for the particular patient, processing continues to 905 where the system can initiate a query or error message to determine why there is not a match. For example, an alarm may sound to alert the operator of treatment device 120 to immediately stop delivery of treatment. As another example, an alert may be forwarded to controller 130 to alert health care providers that an error occurred. Those skilled in the art will recognize that other steps may be taken to ensure that treatment is not delivered and that such an error does not occur in the future.

If processing at 904 indicates that the patient is the intended patient for the treatment to be administered via the treatment device 120, processing continues at 906 where system 100 can, query one or more datastores to receive treatment information for patient 102. In some embodiments, this includes forwarding the patient identifier received at 902 to controller 130. Controller 130 then retrieves treatment information from treatment database 400. In some embodiments, processing at 904 simply involves retrieving treatment data from a memory of treatment device 120.

Processing continues at 908 where the course of treatment specified by the treatment information retrieved at 906 is used to initiate treatment. This may include, for example, utilizing the treatment information retrieved at 906 to manipulate treatment device 120 to deliver a course of treatment. For example, if the treatment is to deliver 50 cc of Penicillin, processing at 908 may include monitoring an intelligent shot while a nurse delivers the prescribed dose of medication. Processing may continue at 910 where system 100 acts to verify the treatment delivered. This may include, for example, recording data at treatment device 120 which reflects the actual treatment delivered and comparing the actual treatment data to the stored treatment data. In some embodiments, processing concludes at 912 where treatment information is updated. For example, this may include updating information at the treatment device 120 and/or information at controller 130 or the like.

Process 900 illustrates a method for confirming a treatment action delivered by a treatment device. The treatment device may be a health care device, and may also be any of a number of other intelligent devices, including, for example, treatment devices, diagnostic devices, nutritional devices, testing and measurement devices, surgical devices, medical devices, and others. By way of example, treatment device 120 might be an intelligent IV needle, which might check a patient identifier transmitted via PAN 104 to confirm that the patient is the intended patient before it will operate to inject a prescribed dosage of medicine. Alternatively, the needle might transmit a message of intended treatment to another network device via PAN 104, which might, by a processor, confirm whether the treatment is appropriate and send a return message to the needle, which could then allow treatment if the patient is in fact the correct patient.

It should be noted that while in some embodiments a patient identifier is transmitted via PAN 104 to a treatment device 120, in some embodiments treatment device 120 may transmit a message or data in the reverse direction, to another device via PAN 104, in which case the network device automatically knows which patient 102 is identified (i.e., the patient for a particular PAN 104). In some embodiments, treatment device 120 may transmit a treatment identifier, or other action identifier or data, which can be matched by a processor of a network device associated with PAN 104 against a record to confirm that the treatment or action is appropriate for that patient. Examples of actions taken by a network device associated with PAN 104 are: to check a proposed treatment against restrictions in the patient's record, to confirm a treatment against a patient's diagnosis, to check for potentially harmful interactions in proposed treatments, and the like.

In some embodiments, other network devices may perform the matching, including devices which are not in communication via the PAN 104 (e.g., controller 130), so that both a patient identifier and an action or treatment identifier are transmitted for matching at the external processor. Thus, the control of the matching of patient to proposed action can be handled at any of the system components, with PAN 104 serving as a vehicle for data communication and also for verifying the correctness of the patient for which the action is proposed.

Figure 10:
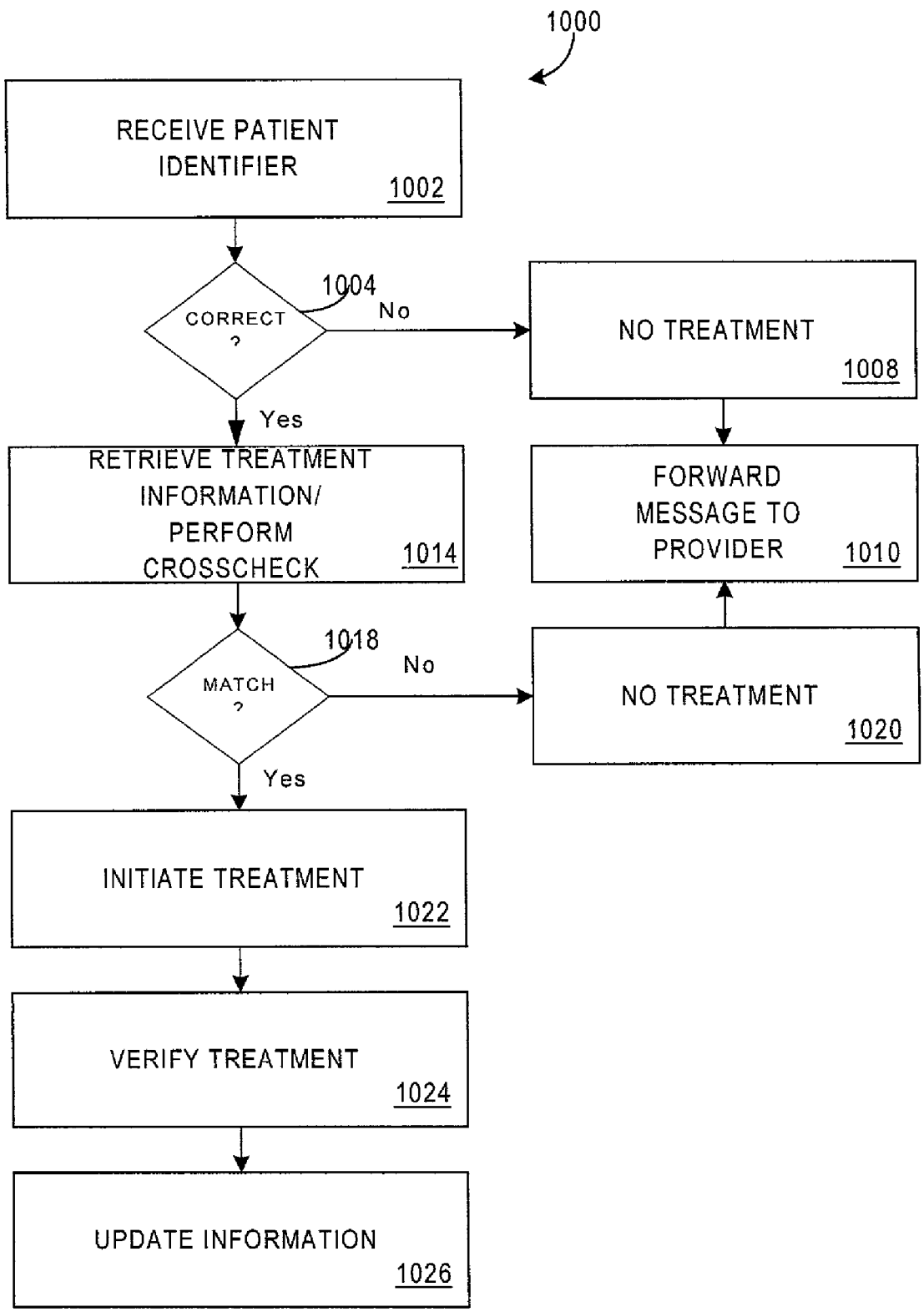
FIG. 10 is a flow diagram depicting a treatment process according to one embodiment of the present invention.

A further embodiment of treatments which may be administered and controlled using system 100 will now be described by referring to FIG. 10, where a treatment process 1000 is shown. Processing begins at 1002 where a network device, such as treatment device 120, receives a patient identifier via Pan 104. For example, a treatment device configured to communicate via PAN 104 may be positioned in proximity to patient 102 and may receive a patient identifier stored at, for example, a transmitter associated with PAN 104. Processing continues at 1004 where a determination is made whether the patient identifier received at 1002 is the correct patient identifier for treatment by a particular device. If the patient identifier is not correct (e.g., is not located within a database of patients to be treated, etc.), processing continues at 1008 and no treatment is delivered. In some embodiments, a message may be delivered at 1010 indicating that no treatment was provided and that an incorrect patient identifier was received.

Processing continues at 1014 where treatment information for the patient identified by patient identifier retrieved at 1002 is retrieved (e.g., this information may be retrieved from memory of the treatment device, from another network device, or from controller 130). In some embodiments, processing at 1014 may also include performing a cross-check to check the proposed action against a criterion for action. For example, the system may cross-check a treatment against a treatment/diagnosis database, to confirm that a treatment action is the right one for the diagnosis that is recorded for patient 102, based on patient information retrieved from patient database 300.

At 1018, a determination is made whether the cross-check finds any problems. For example, if the cross-check finds that a particular type of medication will cause an allergic reaction in a patient, processing at 1018 will indicate that a treatment plan including that particular type of medication should not be delivered, and processing will continue to 1020 where no treatment will be delivered. Error messages, alerts, alarms, or other indications may be presented to the nurse or operator of the treatment device. Further, a message or other information may be transmitted at 1010 to the patient's doctor or other responsible provider.

If the cross-check is successful at 1018 (e.g., no problems or issues are identified with the proposed treatment), then processing continues at 1022 where treatment is initiated. As described above, steps, such as steps 1024 and 1026, may also be included to verify the treatment after it is delivered and to update information after treatment is complete. Optionally, the system may, at any of the steps of the process, record data indicating the outcome of each step, or initiate an interaction with a doctor, nurse, or other health care provider based on the results of the step.

The cross-check application of process 1000 may be conducted under the control of treatment device 120, another network device 108, 112, or under the control of controller 130. In some embodiments, the cross-check can be used to facilitate a universal identifier for use with multiple providers.

To facilitate cross-checking treatments, system 100 may obtain data from sources other than devices in communication with PAN 104. For example, treatment device 120 may include a sensor which obtains data from the patient or from the patient's environment, or by communication, such as from a computer network. Thus, for example, an intelligent needle can read a bar code on a container of medicine, convey a message that the medicine is about to be provided, and receive confirmation as to whether the treatment is allowed for that particular patient (who was identified based on the patient identifier received via PAN 104). This determination may be made by comparing the patient identifier with information about the patient and information about a proposed treatment, and optionally based on the absence of conflict between the proposed treatment and any restrictions, drug interactions, or counter-indications stored for the patient. The result is a system which allows accurate and safe delivery of controlled and monitored treatments.

Figure 11:
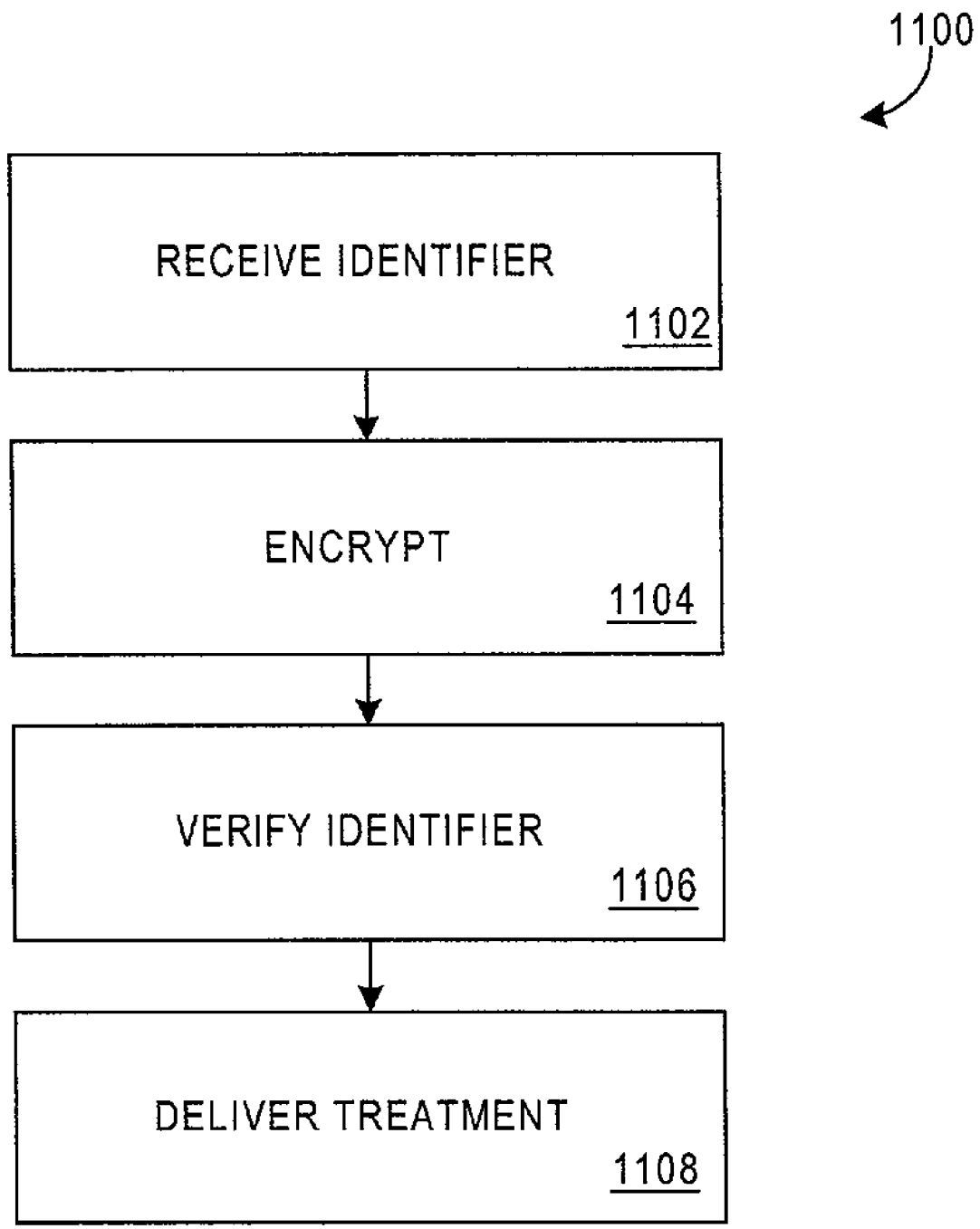
FIG. 11 is a flow diagram depicting a identity obscuring process according to one embodiment of the present invention.

Referring now to FIG. 11, a treatment process 1100 according to some embodiments of the present invention is shown. In some cases it may be appropriate to include a facility for maintaining anonymity of a patient during or after providing a health care service. Process 1100 provides one mechanism for providing such patient anonymity. Processing begins at 1102 where a network device 108, 112 of system 100 receives a patient identifier associated with a particular patient who has a PAN 104 established. The network device which has received this patient identifier, at 1104, encrypts it to obscure the identity of the patient. This encrypted and anonymized patient identifier may then be verified (e.g., by comparing it to stored patient information) and used to identify and then deliver treatment at steps 1106 and 1108 (e.g., as described above in conjunction with FIGS. 9 and 10). The anonymous version of the identifier may be used to identify the patient for record-keeping purposes, such as to record patient data in clinical trials, experiments, or the like. A variety of encryption, anonymizer and other techniques may be used to obscure the patient identity. In some embodiments a handshaking protocol may be used.

Although the present invention has been described with respect to particular embodiments, those skilled in the art will note that various substitutions may be made to those embodiments described herein without departing from the spirit and scope of the present invention.

Disclosed herein are also methods and systems for handling data associated with a patient. For example, methods and systems include associating a patient with a personal area network, recording data associated with the patient, and associating the data with a record for the patient in a database. The data may be communicated via the personal area network among a plurality of health care devices and applications. Data associated with a patient may include blood pressure, temperature, pressure, vapor content, moisture, blood oxygen level, blood content, blood alcohol content, toxicity data, chemical content data, respiration content data, food consumption data, urine content data, waste production data, pulse, respiration rate, EKG data, EEG data, a patient order, a medical record, a diagnosis, and/or a treatment order.

In some embodiments, computer systems may be provided for storing, manipulating, communicating and/or handling data from the personal area network. The computer system may include a server and/or a plurality of client computers. The computer system may be in communication with one or more treatment devices and other network devices via a communications network. The methods and system may further include a security facility for protecting the data, which may include any of an encryption process, an anonymizer and a handshaking protocol. In some embodiments, the methods and systems include an anonymizer for obscuring a patient identifier while allowing access to other data associated with the patient. In some embodiments, an identifier for a patient serves as an identifier for a plurality of health care providers, such as a doctor, a surgeon, a hospital, and an insurance provider.

In some embodiments, the personal area network is generated by a transmitter configured as a small device such as a bracelet, ring, microtransmitter or other device for transmitting data via the electrochemical characteristics of the patient. The methods and systems disclosed herein can also include one or more sensors for sensing a condition of a patient. The sensor can communicate with other devices via the personal area network or another network The sensor can sense any of a wide variety of conditions, such as blood pressure, temperature, pressure, vapor content, moisture, blood oxygen level, blood content, blood alcohol content, toxicity, chemical content, respiration content, food consumption, urine content, waste content, pulse, respiration rate, electrical activity, and others. Encompassed herein are any methods of providing or otherwise establishing a personal area network for health care, including providing a sensor configured to interact with a personal area network to facilitate health care.

In some embodiments, methods and systems for facilitating a health care service are provided, which may include providing a processor for a personal area network, and configuring the processor to facilitate communication with an intelligent health care device or treatment device. The health care device may be a thermometer, an IV, a blood pressure cuff, an EKG, an EEG, a fluid sensor, a food tray, a tray, an operating table, a needle, a patch, a vial, a bottle, a blade, a knife, a scalpel, a clamp, a stent, a prosthesis, a catheter, a tube, an intubator, a medicine bottle, sphygmomenometer, a toxicity screening device, a chemical sensor, a spectrometer, a respiration rate measurement device, an MRI, and a CT device.

In some embodiments, computer network methods and systems are provided which allow communication between devices via a personal area network. In some embodiments, an intelligent device is in communication with other devices via the network. The intelligent device may be any of a thermometer, an IV, a blood pressure cuff, an EKG, an EEG, a fluid sensor, a food tray, a tray, an operating table, a needle, a patch, a vial, a bottle, a blade, a knife, a scalpel, a clamp, a stent, a prosthesis, a catheter, a tube, an intubator, a medicine bottle, sphygmomenometer, a toxicity screening device, a chemical sensor, a spectrometer, a respiration rate measurement device, an MRI, a CT device, or many others. In embodiments a database may be provided for associating a patient identifier with at least one of a treatment, a diagnosis, an event, a reading and a condition. The database may be stored by a process selected from the group consisting of local storage at the processor of the personal area network, storage on a smart card, local storage at a device other than the personal area network, storage on a server, storage on a host computer, and storage on a remote machine.

While the invention has been disclosed in connection with embodiments shown and described in detail, various equivalents, modifications, and improvements will be apparent to one of ordinary skill in the art from the above description.

What is claimed is:

1. A method for delivering a treatment, comprising:
   a patient wearing a first device which is not implanted in the patient;
   bringing a second device in contact with the patient, said second device to selectively apply a proposed treatment to the patient;
   said first device transmitting to said second device a patient identifier via an electrical current signal transmitted via the patient's body, said patient identifier including information for identifying the patient;
   said second device using said transmitted patient identifier to confirm that said proposed treatment is intended for the patient; and
   said second device applying said proposed treatment to the patient after confirming that said proposed treatment is intended for the patient.

2. The method of claim 1, wherein said second device is not implanted in the patient.

3. A method for delivering a treatment, comprising:
   a patient wearing a first device and a third device where the first device is not implanted in the patient;
   said first device transmitting to said third device a patient identifier via an electrical current signal transmitted via the patient's body, said patient identifier including information for identifying the patient;
   bringing a second device in contact with the patient, said second device to selectively apply a proposed treatment to the patient;
   said second device transmitting to said third device a message indicative of said proposed treatment, said message transmitted to said third device from said second device via an electrical current signal transmitted via the patient's body;
   said third device using said transmitted patient identifier and said transmitted message to confirm that said proposed treatment is intended for the patient;
   said third device transmitting a return message to said second device; and
   said second device responding to said return message by applying said proposed treatment to the patient.

4. The method of claim 3, wherein said second device is not implanted in the patient.

5. The method of claim 4, wherein said third device is not implanted in the patient.

6. An apparatus for delivering a treatment, comprising:
   a first device worn by a patient and not implanted in the patient;
   a second device in contact with the patient, said second device to selectively apply a proposed treatment to the patient;
   said first device operative to transmit to said second device a patient identifier via an electrical current signal transmitted via the patient's body, said patient identifier including information for identifying the patient;

said second device operative to:
- use said transmitted patient identifier to confirm that said proposed treatment is intended for the patient; and
- apply said proposed treatment to the patient after confirming that said proposed treatment is intended for the patient.

7. The apparatus of claim 6, wherein said second device is not implanted in the patient.

8. An apparatus for delivering a treatment, comprising:
- a first device worn by a patient and not implanted in the patient;
- a second device in contact with the patient, said second device to selectively apply a proposed treatment to the patient;
- a third device worn by the patient;
- said first device operative to transmit to said third device a patient identifier via an electrical current signal transmitted via the patient's body, said patient identifier including information for identifying the patient;
- said second device operative to transmit to said third device a message indicative of said proposed treatment, said second device operative to transmit said message to said third device via an electrical current signal transmitted via the patient's body;
- said third device operative to:
  - use said transmitted patient identifier and said transmitted message to confirm that said proposed treatment is intended for the patient; and
  - transmit a return message to said second device;
- said second device operative to respond to said return message by applying said proposed treatment to the patient.

9. The apparatus of claim 8, wherein said second device is not implanted in the patient.

10. The apparatus of claim 9, wherein said third device is not implanted in the patient.

* * * * *